United States Patent [19]

Esanu

[11] 4,100,287

[45] Jul. 11, 1978

[54] PYRIMIDINE DERIVATIVE

[75] Inventor: Andre Esanu, Paris, France

[73] Assignee: Societe d'Etudes de Produits Chimiques, Paris, France

[21] Appl. No.: 829,004

[22] Filed: Aug. 30, 1977

[30] Foreign Application Priority Data

Sep. 3, 1976 [GB] United Kingdom ............ 36523/76

[51] Int. Cl.² .................. A61K 31/505; C07D 239/42
[52] U.S. Cl. ....................................... 424/251; 544/330
[58] Field of Search ................ 260/256.4 N; 424/251

[56] References Cited

U.S. PATENT DOCUMENTS

| 3,259,623 | 7/1966 | Kober et al. ................. 260/256.4 N |
| 3,481,932 | 12/1969 | Wagner .......................... 260/256.4 N |
| 3,499,898 | 3/1970 | von Bebenburg et al. ... 260/256.4 N |
| 3,978,055 | 8/1976 | Fauran et al. ................ 260/256.4 N |

*Primary Examiner*—Paul M. Coughlan, Jr.
*Attorney, Agent, or Firm*—Eyre, Mann, Lucas & Just

[57] ABSTRACT

A new pharmaceutical compound having analgesic activity is disclosed. The compound is N-2, 6-dichlorophenyl-2-aminopyrimidine. A method of preparing the compound is also disclosed as is a therapeutic composition which includes the compound.

5 Claims, No Drawings

PYRIMIDINE DERIVATIVE

This invention relates to a new compound which is of interest in the pharmaceutical field, to its preparation and to therapeutic compositions containing it. The new compound is N-2, 6-dichlorophenyl-2-aminopyrimidine, which has the formula

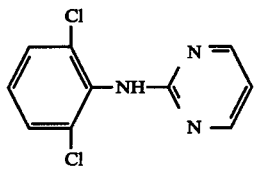

This compound is of interest as it indicates analgesic activity, as has been shown by tests of the pain syndrome using acetic acid (Koster) or phenyl benzoquinone (Siegmund).

The compound of the invention is a yellow crystalline product with the formula $C_{10}H_7Cl_2N_3$ and a melting point of 190° C. It is soluble in chloroform and dimethylsulphoxide at room temperature, but insoluble in water, ethanol and transcutol.

It may be prepared according to this invention by reacting 2, 6-dichloro aniline and 2-chloro pyrimidine, in solution in dimethyl formamide and in the presence of sodium hydride, at a temperature preferably not exceeding 40° C. The reaction proceeds according to the following scheme:

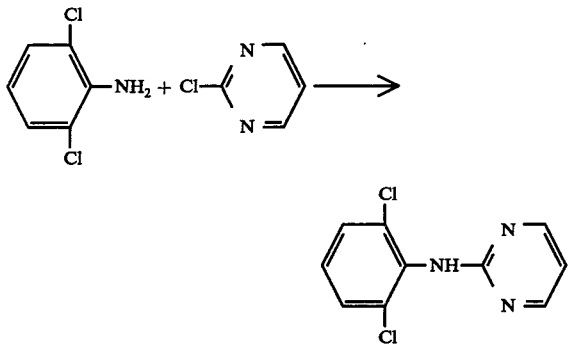

This invention is illustrated by the following Example:

EXAMPLE

In a 2-liter reactor fitted with warming, cooling and stirring means there were poured 250 ml of dimethylformamide and 24.5 g of sodium hydride (0.51 mol). The mixture was warmed to 40°-50° C and there was then added a solution containing, in 300 ml of dimethylformamide 82.6 g (0.51 mol) of 2,6-dichloroaniline. Stirring was maintained for 75 minutes, by which time a brown solution was obtained. This solution was cooled to 20° C and it was slowly added, over a period of 90 minutes, to a solution containing, in 200 ml of dimethyl formamide, 59.5 g (0.51 mol) of 2-chloropyrimidine. During the addition the temperature rose to 35° C.

Stirring was maintained overnight and the dimethylformamide was evaporated. The residue was treated 3 times with isopropyl oxide which led to a pasty product which was washed with water and recrystallized from 300 ml of acetonitrile. After separation and drying there were obtained 61 g (yield 61%) of a yellowish crystalline product melting at 190° C, analysis of which was in agreement with the general formula $C_{10}H_7Cl_2N_3$.

TOXICITY

The per os toxicity has been determined on female mice and rats; on mice the LD 50 is over 6.5 g/Kg and on the rat the LD 50 is 4.72 g/Kg. The compound according to the invention presents accordingly a low toxicity. This has been confirmed by sub-chronic oral administration on the rat.

PHARMACOLOGY

The compound of the invention has been submitted to various tests which have shown a marked analgesic action which has been evidenced by the Koster's test (ED 50 per os 3 mg/Kg) and by the Siegmund's test (ED 50 per os 4.5 mg/Kg). This appears to be an action of the peripheric type and not of the central one, which is an advantage more particularly with respect to secondary effects.

CLINIC

The compound of the invention has been clinically experimented on 21 cases of various pains including 2 cancer cases, 6 members breaks, 3 coxarthrosis.

On those cases, only 1 was not at all affected by treatment, 1 has to be considered as doubtful, 12 were very favourable (strong attenuation of the pain) and 7 resulted in a total cure.

All the patients treated had previously received an other treatment with, in all the cases, quite no result.

Concurrently with the compound of the invention, a placebo preparation was also administered and it has been noticed that in no case, the placebo has had any action.

All the cases treated received 2 or 3 times per diem a gelatine capsule containing 30 mg of active substance. At to the tolerance, no significative phenomenon has been noticed. Duration of the treatments: from 2 to 18 days.

POSOLOGY

The compound according to the invention may be presented in any therapeutically acceptable form such as: tablets, gelatine capsules, suspensions and the like; more particularly the gelatine capsule may be used, each unit containing from 10 to 100 mg of the compound of the invention.

We claim:

1. N-2, 6-dichlorophenyl-2-aminopyrimidine.
2. A process for the preparation of N-2, 6-dichlorophenyl-2-aminopyrimidine comprising the reaction of 2, 6-dichloro aniline and 2-chloro pyrimidine, in solution in dimethyl formamide and in the presence of sodium hydride.
3. The process of claim 2 wherein the temperature is controlled so that it does not exceed 40° C.
4. A therapeutic composition having analgesic activity, said therapeutic composition comprising a carrier and an effective amount of N-2, 6-dichlorophenyl-2-aminopyrimidine.
5. The therapeutic composition of claim 4 wherein the N-2, 6-dichlorophenyl-2-aminopyrimidine is present in the amount of from 10 to 100 mg per dose unit.